US009161986B2

(12) United States Patent
Mizushima et al.

(10) Patent No.: US 9,161,986 B2
(45) Date of Patent: Oct. 20, 2015

(54) NANOPARTICLE CONTAINING PROSTAGLANDIN $I_2$ DERIVATIVE

(75) Inventors: Toru Mizushima, Tokyo (JP); Tsutomu Ishihara, Koriyama (JP); Hongxing Liu, Tokyo (JP)

(73) Assignee: LTT BIO-PHARMA CO., LTD., Tokyo (JP)

( * ) Notice: Subject to any disclaimer, the term of this patent is extended or adjusted under 35 U.S.C. 154(b) by 78 days.

(21) Appl. No.: 13/984,556

(22) PCT Filed: Feb. 13, 2012

(86) PCT No.: PCT/JP2012/053299

§ 371 (c)(1),
(2), (4) Date: Oct. 18, 2013

(87) PCT Pub. No.: WO2012/111627

PCT Pub. Date: Aug. 23, 2012

(65) Prior Publication Data

US 2014/0050690 A1 Feb. 20, 2014

(30) Foreign Application Priority Data

Feb. 18, 2011 (JP) ................................ 2011-033290

(51) Int. Cl.

| | |
|---|---|
| ***A61K 31/5585*** | (2006.01) |
| ***A61K 9/51*** | (2006.01) |
| ***A61K 47/34*** | (2006.01) |
| ***A61K 47/48*** | (2006.01) |
| ***A61K 47/30*** | (2006.01) |
| ***A61K 31/343*** | (2006.01) |

(52) U.S. Cl.

CPC ............ *A61K 47/48215* (2013.01); *A61K 9/51* (2013.01); *A61K 31/343* (2013.01); *A61K 31/5585* (2013.01); *A61K 47/30* (2013.01); *A61K 47/34* (2013.01); *A61K 47/482* (2013.01); *A61K 47/48915* (2013.01)

(58) Field of Classification Search

None

See application file for complete search history.

(56) References Cited

U.S. PATENT DOCUMENTS

| | | | |
|---|---|---|---|
| 2009/0317479 | A1 | 12/2009 | Ishihara et al. |
| 2010/0129456 | A1 | 5/2010 | Ishihara et al. |

FOREIGN PATENT DOCUMENTS

| | | | |
|---|---|---|---|
| EP | 1 479 383 | A1 | 11/2004 |
| EP | 2 361 918 | A1 | 8/2011 |
| JP | 2006-528969 | A | 12/2006 |
| WO | WO-2007/074604 | A1 | 7/2007 |
| WO | WO-2008/139804 | A1 | 11/2008 |
| WO | WO-2010/058669 | A1 | 5/2010 |

OTHER PUBLICATIONS

Kurihara et al., Br J Pharmacol 99: 91-96 (1990).*

International Search Report and Written Opinion dated May 1, 2012 in PCT/JP2012/053299 filed Feb. 13, 2012.

* cited by examiner

*Primary Examiner* — Sue Liu
*Assistant Examiner* — Thor Nielsen
(74) *Attorney, Agent, or Firm* — Drinker Biddle & Reath LLP

(57) ABSTRACT

There is provided a beraprost sodium-containing nanoparticle that contains beraprost sodium among other prostaglandin $I_2$ (prostacyclin) derivatives, which are therapeutic agents for pulmonary hypertension. The beraprost sodium-containing nanoparticle is obtained by making beraprost sodium hydrophobic using a metal ion and allowing the hydrophobic beraprost sodium to react with poly-L-lactic acid or a poly(L-lactic acid/glycolic acid) copolymer, and a poly-DL- or L-lactic acid-polyethylene glycol block copolymer or a poly(DL- or L-lactic acid/glycolic acid)-polyethylene glycol block copolymer. The beraprost sodium-containing nanoparticle excels in sustained release of an active ingredient, reduces a side effect, and furthermore, has an excellent drug retention in the blood. Therefore, the beraprost sodium-containing nanoparticle is quite outstanding particularly regarding the sustainability of the medicinal effect.

18 Claims, 5 Drawing Sheets

NANOPARTICLE CONTAINING PROSTAGLANDIN $I_2$ DERIVATIVE

CROSS REFERENCE TO RELATED APPLICATIONS

This application is a National Stage of International Application No. PCT/JP2012/053299 filed Feb. 13, 2012, and which claims benefit of Japanese Patent Application No. 2011-033290 filed Feb. 18, 2011, which are incorporated herein in their entirety.

TECHNICAL FIELD

The present invention relates to prostaglandin $I_2$ derivative-containing nanoparticles. Specifically, the present invention relates to a beraprost sodium-containing nanoparticle, wherein beraprost sodium is a prostaglandin $I_2$ derivative.

BACKGROUND ART

Pulmonary hypertension is a disease resulting from increased blood pressure in the pulmonary artery (pulmonary arterial pressure) that is caused by blood flow damaged by a stenosis of the lumen of a pulmonary arteriolar located in the periphery of the vessel for sending blood from the heart to the lungs (pulmonary artery).

The treatment of this disease is performed by administration of a pulmonary vasodilator, which secures blood flow and reduces the pulmonary arterial pressure, thereby reducing the workload of a dilated heart or a thickened pulmonary vessel. Various prostaglandin $I_2$ (prostacyclin) derivatives are clinically used.

The first pharmaceutical agent whose clinical application became possible is epoprostenol, which is prostaglandin $I_2$ (prostacyclin) derivatives. Epoprostenol is a biosynthesized form of a substance that naturally occurs in the living body and has a pulmonary vasodilation effect. Prostacyclin activates adenyl cyclase via a prostacyclin receptor on vascular smooth muscle and increases the concentration of cAMP, and thereby relaxes the vascular smooth muscle and exerts the pulmonary vasodilation effect.

Furthermore, this pharmaceutical agent is believed to have an antiplatelet effect and a growth inhibitory effect on smooth muscle as well. In previous studies, the three-year survival rate for an untreated primary pulmonary hypertension group was about 40%, while that for a group treated with epoprostenol was about 70%. This demonstrates that epoprostenol improved a vital prognosis remarkably. Thus, the therapeutic effect of this pharmaceutical agent may be considered practically established.

The above-mentioned epoprostenol has a very short half-life in blood of about 2 to 3 minutes. Furthermore, epoprostenol has a chemical half-life of only about 10 minutes, wherein the chemical half-life serves as a measure of chemical stability. Therefore, a continuous intravenous administration of epoprostenol is required to achieve a stable therapeutic effect. Additionally, at the time of its administration, the continuous intravenous administration has to be performed by dissolving epoprostenol using a liquid to dissolve it and by using a combination of a special catheter that is inserted into a central vein and an infusion pump. This infusion pump (small precision pump for infusion of a pharmaceutical agent) can secure administration rate of 2 ng/kg epoprostenol per one minute. Therefore, epoprostenol is a pharmaceutical agent that gives a highly negative impact to a patient's QOL.

However, the therapeutic effect of epoprostenol on pulmonary hypertension is very remarkable. Accordingly, various prostacyclin derivatives have been recently under development, and development of more stable prostaglandin $I_2$ (prostacyclin) derivatives has been under investigation. As a result, beraprost sodium, which has a relatively long half-life, has appeared as one of the more stable derivatives.

The above-mentioned beraprost sodium is a prostacyclin derivative developed in Japan. Beraprost sodium has a great advantage over other prostacyclin derivatives in that it has a biological half-life of about 1.1 hours and moreover a long chemical half-life of about 10 days, and its oral administration is possible.

Beraprost sodium was originally approved as a therapeutic agent for arteriosclerosis obliterans. Later, clinical trials for primary pulmonary hypertension and pulmonary hypertension that developed as a complication of a collagen disease were performed, and it was found that treatment by administrating beraprost sodium for three months significantly decreased the pulmonary vascular resistance. Consequently, beraprost sodium was approved as a therapeutic agent for primary pulmonary hypertension and presently is widely used as a first-line drug for pulmonary hypertension.

However, a prostacyclin-based pharmaceutical agent tends to show its vasodilation effect relatively concentration-dependently, based on the experiences of using epoprostenol as a therapeutic agent for continuous intravenous infusion. Therefore, in order to achieve a sufficient therapeutic effect, it is necessary to keep the blood concentration of beraprost sodium stable and as high as possible.

It has been published that the time to reach the maximum blood concentration (Tmax) is 1.42 hours and the maximum blood concentration (Cmax) is 440 pg/mL after conventional oral administration of 100 μg of a beraprost formulation. Therefore, although the blood concentration of beraprost sodium increases relatively rapidly and its vasodilation effect is exerted after this pharmaceutical agent is taken, its medicinal effect disappears quickly since the half-life of the blood concentration is only 1.1 hours, which is problematic. Furthermore, since an increased blood concentration of this pharmaceutical agent leads to a side effect such as decreased blood pressure, an intravenous administration that was expected to be efficacious was not possible.

Therefore, there is an urgent need to develop a formulation that keeps a sufficient and lasting blood concentration of beraprost sodium for a long time.

Aside from this, the present inventors have previously carried out various studies aimed at encapsulating a drug in a microparticle or a nanoparticle made by using a poly(lactic acid/glycolic acid) copolymer (that may also be referred to as "PLGA" hereinafter) or a poly lactic acid (that may also be referred to as "PLA" hereinafter).

For example, the present inventors have applied a patent relating to a drug-containing nanoparticle that excels in the targeting of an affected area and sustained release, and moreover, that reduces hepatic accumulation of the drug and enhances the drug retention in the blood (Patent Literature 1). This drug-containing nanoparticle is obtained by making a low molecular weight drug with a negatively charged group hydrophobic using a metal ion and allowing the hydrophobic drug to react with a poly lactic acid-polyethylene glycol block copolymer or a poly(lactic acid/glycolic acid)-polyethylene glycol block copolymer, and a poly lactic acid or a poly(lactic acid/glycolic acid) copolymer, thereby encapsulating the drug into the resultant nanoparticle.

Furthermore, the present inventors improved the above-mentioned technique further and have provided a nanoparticle containing a low molecular weight drug with a negatively charged group, wherein the nanoparticle excels in sustained release. This nanoparticle targets the low molecular weight drug with a negatively charged group to an affected area efficiently, excels in sustained release of the drug, and reduces the side effect of the drug by reducing its hepatic accumulation (Patent Literature 2).

The present inventors assumed that such a nanoparticle formulation that is obtained by applying the techniques described in these patent literatures to a prostaglandin $I_2$ (prostacyclin) derivative and making a nanoparticle containing it would excel in sustained release of the drug and keep a lasting blood concentration of the drug. Thus, the present inventors investigated the preparation of a nanoparticle of a prostaglandin $I_2$ (prostacyclin) derivative.

Consequently, the present inventors successfully prepared a nanoparticle of beraprost sodium highly efficiently, although they failed in preparing a nanoparticle of epoprostenol, which is an early therapeutic agent used for pulmonary hypertension. The present inventors confirmed that the obtained nanoparticle excelled in sustained release of the beraprost sodium encapsulated in the particle and had the drug retantion in the blood, and therefore led to a continuous onset of a pharmacological effect, thereby accomplishing the present invention.

PRIOR ART DOCUMENTS

Patent Documents

Patent Document 1: International Publication NO. WO 2007/074604 A1

Patent Document 2: International Publication NO. WO 2008/139804 A1

SUMMARY OF THE INVENTION

Problems to be Solved by the Invention

Therefore, it is an object of the present invention to provide a nanoparticle that contains beraprost sodium among other prostaglandin $I_2$ (prostacyclin) derivatives, which are therapeutic agents for pulmonary hypertension.

Means for Solving the Problem

The present invention solves the above-mentioned problems and specifically includes the following embodiments.

(1) Thus, a basic embodiment of the present invention is a beraprost sodium-containing nanoparticle obtained by making beraprost sodium represented by the following formula (I):

[Chemical formula 1]

(I)

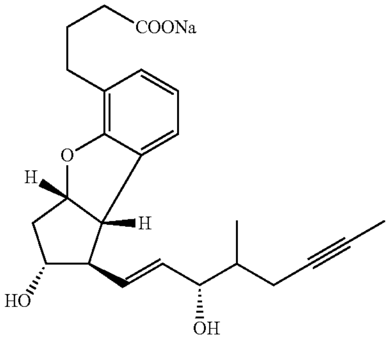

hydrophobic using a metal ion and allowing the hydrophobic beraprost sodium to react with poly-L-lactic acid or a poly(L-lactic acid/glycolic acid) copolymer, and a poly-DL- or L-lactic acid-polyethylene glycol block copolymer or a poly(DL- or L-lactic acid/glycolic acid)-polyethylene glycol block copolymer.

More specifically, the present invention includes the following configurations.

(2) the beraprost sodium-containing nanoparticle according to the above-mentioned (1) in which a basic low molecular weight compound is further mixed;

(3) the beraprost sodium-containing nanoparticle according to the above-mentioned (1) or (2), wherein the particle has a diameter of 20 to 300 nm, preferably 50 to 200 nm;

(4) the beraprost sodium-containing nanoparticle according to the above-mentioned (1) or (2), wherein the metal ion is one or two or more of an iron ion, a zinc ion, a copper ion, a magnesium ion, a calcium ion, a nickel ion, a beryllium ion, a manganese ion, or a cobalt ion;

(5) the beraprost sodium-containing nanoparticle according to the above-mentioned (1) or (2), wherein the weight average molecular weight of the poly-DL- or L-lactic acid-polyethylene glycol block copolymer or the poly(DL- or L-lactic acid/glycolic acid)-polyethylene glycol block copolymer is 3,000 to 30,000;

(6) the beraprost sodium-containing nanoparticle according to the above-mentioned (2), wherein the basic low molecular weight compound is one or two or more selected from (dimethylamino)pyridine, pyridine, piperidine, pyrimidine, pyrazine, pyridazine, quinoline, quinuclidine, isoquinoline, bis(dimethylamino)naphthalene, naphthylamine, morpholine, amantadine, aniline, spermine, spermidine, hexamethylenediamine, putrescine, cadaverine, phenethylamine, histamine, diazabicyclooctane, diisopropylethylamine, monoethanolamine, diethanolamine, triethanolamine, ethylamine, diethylamine, triethylamine, methylamine, dimethylamine, trimethylamine, triethylenediamine, diethylenetriamine, ethylenediamine, and trimethylenediamine;

(7) a formulation for parenteral administration in the form of an intravenous injection formulation or a local injection formulation that includes the beraprost sodium-containing nanoparticle according to the above-mentioned (1) to (6) as an active ingredient.

Advantageous Effects of Invention

The beraprost sodium-containing nanoparticle provided by the present invention (that may also be referred to as a beraprost nanoparticle hereinafter) targets beraprost sodium as an active ingredient to an affected area, excels in sustained release of the active ingredient, reduces a side effect, and furthermore, has an excellent drug retention in the blood. The beraprost sodium-containing nanoparticle is quite outstanding particularly regarding the sustainability of the medicinal effect.

Therefore, a therapeutic agent for pulmonary hypertension that has both an excellent sustainability of the medicinal effect and a good drug retention in the blood, and has consideration for QOL of a patient can be provided by preparing a nanoparticle of beraprost sodium having a relatively short half-life. The industrial applicability of the beraprost sodium-containing nanoparticle is great.

EMBODIMENTS FOR CARRYING OUT THE INVENTION

Figure 1:
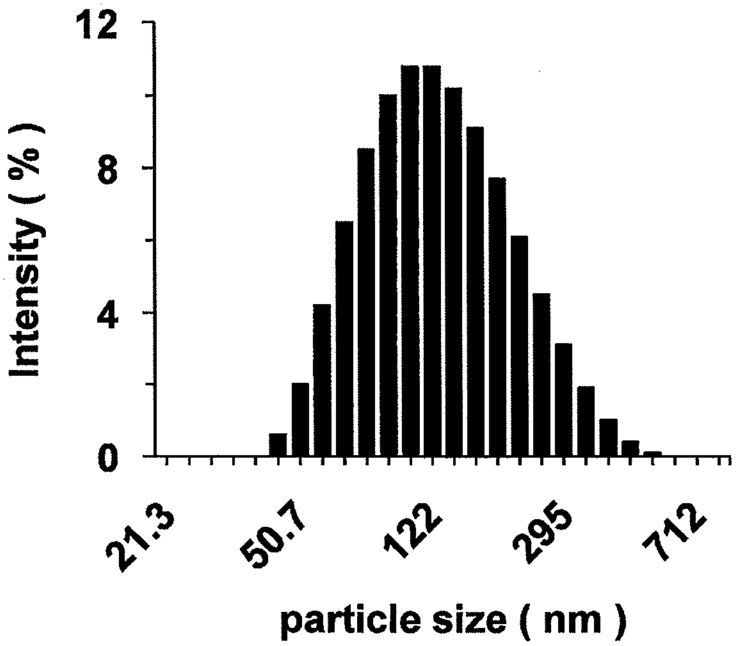
FIG. 1 shows the distribution of the mean particle size of the beraprost sodium nanoparticles of the present invention in Example 2.

The beraprost sodium-containing nanoparticle provided by the present invention is prepared as an insoluble precipitate (complex) of the beraprost sodium by making beraprost sodium hydrophobic using a metal ion and obtained by allowing the insoluble complex to react with poly-L-lactic acid or a poly(L-lactic acid/glycolic acid) copolymer, and a poly-DL- or L-lactic acid-polyethylene glycol block copolymer or a poly(DL- or L-lactic acid/glycolic acid)-polyethylene glycol block copolymer. Furthermore, a surfactant may be added to the nanoparticle. The generated nanoparticle can be stabilized by adding the surfactant.

It is also one of the characteristics of the beraprost sodium-containing nanoparticle provided by the present invention to use poly-L-lactic acid (L-isomer) or a poly(L-lactic acid/glycolic acid) copolymer (L-isomer) as a biodegradable polymer used for forming a nanoparticle.

Poly-L-lactic acid is known to have a different solubility in an organic solvent and a higher crystallinity compared to poly-DL-lactic acid. In the present invention, poly-L-lactic acid is mixed with a poly-DL- or L-lactic acid-polyethylene glycol block copolymer or a poly(DL- or L-lactic acid/glycolic acid)-polyethylene glycol block copolymer to form a nanoparticle. In this manner, crystallization of poly-L-lactic acid in the aqueous phase is suppressed and a stably dispersible nanoparticle can be prepared.

Since poly-L-lactic acid is insoluble in acetone, a nanoparticle was prepared by using a liquid mixture of acetone and dioxane or acetone and tetrahydrofuran to increase the solubility of poly-L-lactic acid.

The above-mentioned beraprost sodium-containing nanoparticle may also include a surfactant. Addition of the surfactant can lead to stabilization of the generated nanoparticle and suppression of the aggregation of the particles.

The beraprost sodium-containing nanoparticle of the present invention provided as described above can be administered in the form of a formulation for parenteral administration, such as an intravenous injection formulation and a local injection formulation.

Particularly, the beraprost sodium-containing nanoparticle is exceptionally unique in that it can be administered intravenously and overcome the disadvantage of a conventional beraprost sodium formulation that was prepared only as an oral administration formulation and whose continuous administration was impossible.

Furthermore, the presence of a metal ion, preferably an iron ion is essential for preparing a nanoparticle of beraprost sodium, an active ingredient in the context of the present invention. The presence of the iron ion enabled preparation of an insoluble complex, and consequently enabled preparation of the nanoparticle.

In this respect, the present invention is exceptionally unique.

The beraprost sodium-containing nanoparticle provided by the present invention can be produced as follows.

Namely, the beraprost sodium-containing nanoparticle can be prepared by mixing beraprost sodium and a metal ion, preferably an iron ion in a solvent such as an organic solvent or a hydrous organic solvent to generate a hydrophobic drug, adding poly-L-lactic acid or a poly(L-lactic acid/glycolic acid) copolymer, and moreover a poly-DL- or L-lactic acid-polyethylene glycol block copolymer or a poly(DL- or L-lactic acid/glycolic acid)-polyethylene glycol block copolymer into this liquid mixture and stirring the mixture, and adding the obtained solution into water to allow the solution to diffuse in the water.

Alternatively, a similar nanoparticle can also be prepared by combining simultaneously a solution obtained by dissolving poly-L-lactic acid or a poly(L-lactic acid/glycolic acid) copolymer and moreover a poly-DL- or L-lactic acid-polyethylene glycol block copolymer or a poly(DL- or L-lactic acid/glycolic acid)-polyethylene glycol block copolymer in a solvent, an aqueous solution of a low molecular weight drug with a negatively charged group, and an aqueous solution of a metal ion and mixing them.

The use of a poly-DL- or L-lactic acid-polyethylene glycol block copolymer or a poly(DL- or L-lactic acid/glycolic acid)-polyethylene glycol block copolymer as a surface modifier for a nanoparticle can suppress crystallization of poly-L-lactic acid or a poly(L-lactic acid/glycolic acid) copolymer in the aqueous phase. Consequently, a stable nanoparticle with an uniform particle size can be obtained.

A metal ion that is used is any of a zinc ion, an iron ion, a copper ion, a nickel ion, a beryllium ion, a manganese ion, and a cobalt ion. One or two or more of water-soluble metal salts thereof are used. Among them, a zinc ion and an iron ion are preferred. Thus, zinc chloride, iron chloride, and the like may be preferably used.

Especially, it was found that beraprost sodium formed an insoluble complex (precipitate) for the first time when iron chloride was used.

The solvent used for the reaction described above is an organic solvent, such as acetone, acetonitrile, ethanol, methanol, propanol, dimethylformamide, dimethyl sulfoxide, dioxane, and tetrahydrofuran, or hydrous solvents thereof. Acetone, dimethylformamide, dioxane, and tetrahydrofuran are preferred.

A poly-DL- or L-lactic acid-polyethylene glycol block copolymer (a DL-isomer may also be referred to as PDLLA-PEG, and an L-isomer may also be referred to as PLLA-PEG) or a poly(DL- or L-lactic acid/glycolic acid)-polyethylene glycol block copolymer (a DL-isomer may also be referred to as PDLLGA-PEG, and an L-isomer may also be referred to as PLLGA-PEG) can be generated by allowing poly-DL-lactic acid (that may also be referred to as PDLLA) or poly-L-lactic acid (that may also be referred to as PLLA), or a poly(DL-lactic acid/glycolic acid) copolymer (that may also be referred to as PDLLGA) or a poly(L-lactic acid/glycolic acid) copolymer (that may also be referred to as PLLGA)(these polymers are referred to as block A) to react with polyethylene glycol (that may also be referred to as PEG)(this is referred to as block B) in the presence of a condensing agent such as ethylene dimethylaminopropyl carbodiimide. However, commercially available similar block copolymers may be used.

The object of the present invention can be achieved regardless of the structure of the block copolymer, wherein the structure may be any of an A-B type, an A-B-A type, and a B-A-B type. Furthermore, the weight average molecular weight of these block copolymers is preferably 3,000 to 30,000.

Furthermore, in the context of the beraprost sodium-containing nanoparticle of the present invention, a higher mixing ratio of poly-L-lactic acid or a poly(L-lactic acid/glycolic acid) copolymer to a poly-DL- or L-lactic acid-polyethylene glycol block copolymer or a poly(DL- or L-lactic acid/glycolic acid)-polyethylene glycol block copolymer tends to result in generation of a bigger nanoparticle and a higher encapsulation efficiency of the drug into the nanoparticle.

Mixing a basic low molecular weight compound additionally in the beraprost sodium-containing nanoparticle provided by the present invention increases the encapsulation efficiency of beraprost sodium into the nanoparticle. The encapsulation efficiency can increase up to about 10%.

Examples of such basic low molecular weight compounds may include (dimethylamino)pyridine, pyridine, piperidine, pyrimidine, pyrazine, pyridazine, quinoline, quinuclidine, isoquinoline, bis(dimethylamino)naphthalene, naphthylamine, morpholine, amantadine, aniline, spermine, spermidine, hexamethylenediamine, putrescine, cadaverine, phenethylamine, histamine, diazabicyclooctane, diisopropylethylamine, monoethanolamine, diethanolamine, triethanolamine, ethylamine, diethylamine, triethylamine, methylamine, dimethylamine, trimethylamine, triethylenediamine, diethylenetriamine, ethylenediamine, trimethylenediamine, and the like. Secondary or tertiary amines are preferably used and diethanolamine is particularly preferred.

The beraprost sodium-containing nanoparticle thus prepared may also include a surfactant. Addition of the surfactant can lead to stabilization of the generated nanoparticle and suppression of the aggregation of the particles. Therefore, addition of the surfactant is favorable for the formulation process of a nanoparticle-containing formulation.

Examples of the surfactants that are used may include phosphatidylcholine, polyoxyethylene (20) sorbitan monooleate, polyoxyethylene (20) sorbitan monolaurate, polyoxyethylene (20) sorbitan monostearate, polyoxyethylene (20) sorbitan monopalmitate, polyoxyethylene (20) sorbitan trioleate, polyoxyethylene(80) octylphenyl ether, polyoxyethylene (20) cholesterol ester, lipid-polyethylene glycol, polyoxyethylene hydrogenated castor oil, a fatty acid-polyethylene glycol copolymer, and the like. Preferably, one or two or more selected from these surfactants are used.

The beraprost sodium-containing nanoparticles provided by the present invention have a mean particle size of the particles in the range of 20 to 300 nm, preferably of 50 to 200 nm, and more preferably of around 120 nm.

The particle size can be adjusted by controlling the amount of the solvent, which is preferably acetone or dioxane, to dissolve PDLLA-PEG or PLLA-PEG, or PDLLGA-PEG or PLLGA-PEG. A nanoparticle with a smaller particle size can be obtained by increasing the amount of acetone or dioxane. Furthermore, a nanoparticle with a larger particle size tends to achieve a higher encapsulation efficiency of the drug.

The beraprost sodium-containing nanoparticle of the present invention prepared as described above is collected and stored after the solution or the suspension of the nanoparticles is purified as appropriate by a process such as centrifugation, ultrafiltration, gel filtration, filtration by means of a filter, and fiber dialysis, and then freeze-dried.

In such a case, a stabilizing agent and/or a dispersing agent are preferably added during the freeze-drying process so that the freeze-dried formulation can be resuspended and administered. Sucrose, trehalose, carboxymethylcellulose sodium, and the like are preferably used as such a stabilizing agent and/or a dispersing agent.

The beraprost sodium-containing nanoparticle provided by the present invention is used as a medicament in the form of a formulation for parenteral administration, such as an intravenous injection formulation and a local injection formulation. Particularly, it has become possible to formulate beraprost sodium, which was conventionally administered orally, as an intravenous injection formulation, and therefore, the nanoparticle of interest can demonstrate its characteristics and efficacy more effectively.

Examples of bases and other additive ingredients used for preparation of these formulations for parenteral administration may include various pharmaceutically accepted and used bases and ingredients. Specifically, saline, saccharides, such as monosaccharides, disaccharides, sugar alcohols, and polysaccharides; polymer additives, such as hydroxyethylcellulose, hydroxypropylcellulose, and methylcellulose; an ionic surfactant or a nonionic surfactant, and the like can be selected and used as appropriate depending on the dosage form.

EXAMPLES

The present invention will now be described in further detail with reference to Examples, but the present invention is not limited to these Examples.

Example 1

Synthesis of Poly-L-Lactic Acid-Polyethylene Glycol Block Copolymer (PLLA-PEG)

Forty grams of methoxy-PEG (Mw 5200, manufactured by NOF Corporation), 40 g of L-lactide (manufactured by Purac), and tin octylate (400 mg) were placed in a two-necked round-bottom flask and mixed thoroughly. The mixture was degassed by an oil hydraulic pump and then was melted by heating it in an oil bath at 110° C. Once melted, the temperature was raised to 155° C. and the mixture was allowed to react for 4 hours. The reaction product (solid) was cooled and then dissolved in about 250 mL of dichloromethane. The solution was then purified through reprecipitation by adding it slowly to 2.5 L of ice-cooled isopropanol, and the purified product was freeze-dried. In this manner, a poly-L-lactic acid-polyethylene glycol block copolymer (PLLA-PEG) was synthesized. The synthesized product was evaluated by gel filtration chromatography (GPC) or proton NMR.

The GPC analysis showed an increased molecular weight compared to methoxy-PEG, and the proton NMR analysis confirmed the presence of poly lactic acid, suggesting that the synthesized product was PLLA-PEG. Furthermore, the same procedure as described above was performed using a different amount of L-lactide to obtain PLLA-PEG with a different molecular weight.

Example 2

Production Method of Nanoparticle Composed of PLA and PDLLA-PEG that Encapsulated Beraprost Sodium (Production Through Diffusion in Solvent)

Twenty six milligrams of PLA (manufactured by Taki Chemical Co., Ltd.) was dissolved in 300 μL of dioxane. Twenty four milligrams of PLLA-PEG synthesized in Example 1 was dissolved in 500 μL of acetone and was mixed with the above-mentioned dioxane solution.

To this liquid mixture, 700 μL of a mixed solution of dioxane and methanol in which 2.5 mg of beraprost sodium was dissolved was added, and subsequently, 200 μL of acetone solution in which 9.5 mg of diethanolamine was dissolved was added. Immediately, a solution of 2.4 mg of anhydrous ferric chloride in 200 μL of acetone was added to and mixed with the above mixture. This mixture was allowed to stand for 10 minutes at room temperature.

The above-mentioned reaction liquid was slowly added dropwise using a 3 mL syringe fitted with a 26G injection needle into 25 mL of water placed in a 50 mL sample vial, with stirring with a 2 cm stirrer bar (stirrer rotation speed: 1000 rpm, injection needle: 26G, syringe: 3 mL syringe manufactured by NIPRO CORPORATION, dropping speed: 48 L/hr). To the resulting suspension, 2.5 mL of a 500 mM EDTA aqueous solution (pH 7) and 12 μL of a 200 mg/mL Tween 80 (polyoxyethylene (20) sorbitan monooleate) aqueous solution were added. After the mixture was concentrated by ultrafiltration (YM-50, manufactured by Amicon Corporation), a 50 mM EDTA aqueous solution (pH 7) was added and the mixture was concentrated again (this process was repeated twice). The obtained concentrated suspension was sonicated for 30 seconds and then aggregates were removed by centrifugation (1000 rpm, 5 minutes). Then, the particle size was measured on a dynamic light scattering analyzer, and the amount of beraprost sodium encapsulated in a particle was determined by HPLC.

One example of the amounts of the respective ingredient to be mixed according to the above-mentioned formulation is shown in Table 1 below. It goes without saying that a formulation is not limited to this formulation.

TABLE 1

| Ingredient | | Solvent | |
|---|---|---|---|
| PLA | 26 mg | Dioxane | 300 μL |
| PLLA-PEG | 24 mg | Acetone | 500 μL |
| beraprost sodium | 2.5 mg | Dioxane/Acetone | 700 μL |
| Anhydrous Ferric chloride | 2.4 mg | Acetone | 30 μL |
| Diethanolamine | 9.5 mg | Acetone | 200 μL |
| Total amount of Solvents | | About 1.7 mL | |

Mean Particle Size, Encapsulation Efficiency, and Recovery Rate of Nanoparticles The distribution of the particle size, the encapsulation efficiency, and the recovery rate of the obtained beraprost sodium-containing nanoparticles are shown below.

FIG. 1 shows the distribution of the mean particle size of the beraprost sodium-containing nanoparticles. Table 2 below shows the encapsulation efficiency and the recovery rate of beraprost sodium in the beraprost sodium-containing nanoparticles.

TABLE 2

| PLA | Mean particle size | beraprost sodium | |
|---|---|---|---|
| (MW: kDa) | (nm) | Encapsulation (%) | Recovery rate (%) |
| PLLA (20) | 128 ± 3 | 1.08 ± 0.04 | 8.76 ± 0.68 |

In the case of the beraprost sodium-containing nanoparticle provided by the present invention, it was possible to produce a nanoparticle with a mean particle size of 120 nm, an encapsulation efficiency of 1%, and a recovery rate of 9% with high reproducibility.

Example 3

Formation of Insoluble Complex in the Presence of Ferric Chloride

It was found about the beraprost sodium-containing nanoparticle of the present invention that beraprost sodium formed an insoluble complex for the first time in the presence of ferric chloride and as a result, a nanoparticle could be produced efficiently.

Thus, beraprost sodium was encapsulated in a nanoparticle through interaction with ferric chloride.

To confirm this, the pH change of the solution and the percentage of beraprost sodium remaining in its supernatant when various amounts of diethanolamine (DEA) was added to the solution in the presence or absence of ferric chloride were examined.

Specifically, the pH of the solution was adjusted by adding diethanolamine to the aqueous solution of an iron ion of a specific concentration (455 mM) and beraprost sodium (32.5 mM) so that various pHs of the solution were obtained. The solution (suspension) was centrifuged at 16,500 g for 10 minutes, and the amount of beraprost sodium dissolved in the supernatant was determined by HPLC. The pH of the solution was also measured.

On the other hand, the pH of the solution was adjusted by adding diethanolamine to the aqueous solution of beraprost sodium (32.5 mM) in which hydrochloric acid was used instead of an iron ion of a specific concentration so that various pHs of the solution were obtained. The solution (suspension) was centrifuged at 16,500 g for 10 minutes, and the amount of beraprost sodium dissolved in the supernatant was determined by HPLC. The pH of the solution was also measured.

Figure 2:
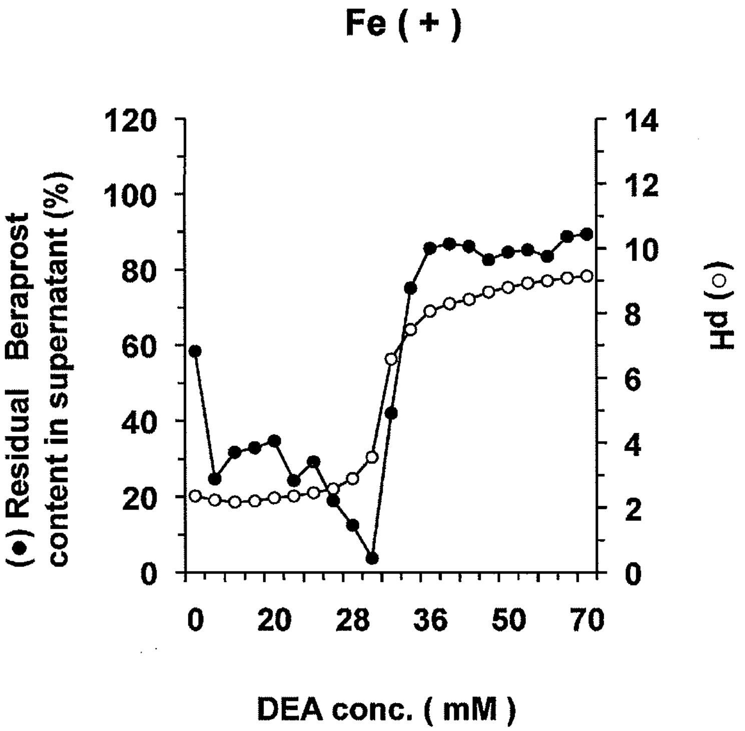
FIG. 2 shows the percentage of remaining beraprost sodium in the presence of ferric chloride in Example 3.
Figure 3:
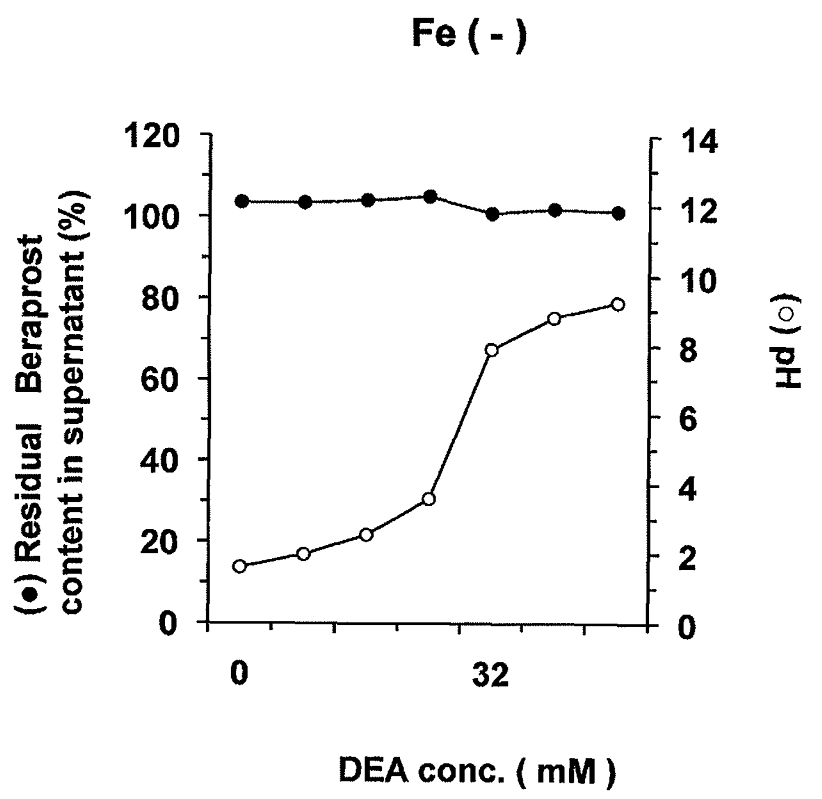
FIG. 3 shows the percentage of remaining beraprost sodium in the absence of ferric chloride in Example 3.

The results are shown in FIG. 2 and FIG. 3.

FIG. 2 shows the pH change of the solution and the percentage of beraprost sodium remaining in its supernatant when various amounts of diethanolamine were added to the solution in the presence of ferric chloride. This result confirmed formation of an insoluble complex, and therefore, it is understood that the presence of ferric chloride is important for preparation of the nanoparticle of the present invention.

On the other hand, FIG. 3 shows the pH change of the solution and the percentage of beraprost sodium remaining in its supernatant when various amounts of diethanolamine was added to the solution in the absence of ferric chloride. This result shows that no insoluble complex was formed.

Example 4

In Vitro Stability of Beraprost Sodium-Containing Nanoparticle

Fifty microliters of fetal bovine serum (FBS), 1 μL of penicillin-streptomycin solution, and 5 μL, of phosphatebuffered saline were added to 45 μL of the suspension of beraprost sodium nanoparticles. After thorough mixing, 100 μL of the mixture was dispensed in a microfuge tube. Then, the sample solution was allowed to stand in a 37° C. incubator, and samples were collected every day.

FBS was used to mimic the in vivo environment.

After sampling, 900 μL of 50 mM phosphate buffer (pH 7) was added to the sample solution, and the mixture was subjected to ultracentrifugation (30,000 rpm, 4° C., and 30 minutes). After ultracentrifugation, the supernatant was removed. One milliliter of ultrapure water was added to the precipitate and the mixture was subjected to ultracentrifugation as well. The precipitate after the removal of the supernatant was used as a sample for determining beraprost sodium.

Determination of beraprost sodium was performed by using the procedures described in the section of the method to measure an encapsulation efficiency.

Figure 4:
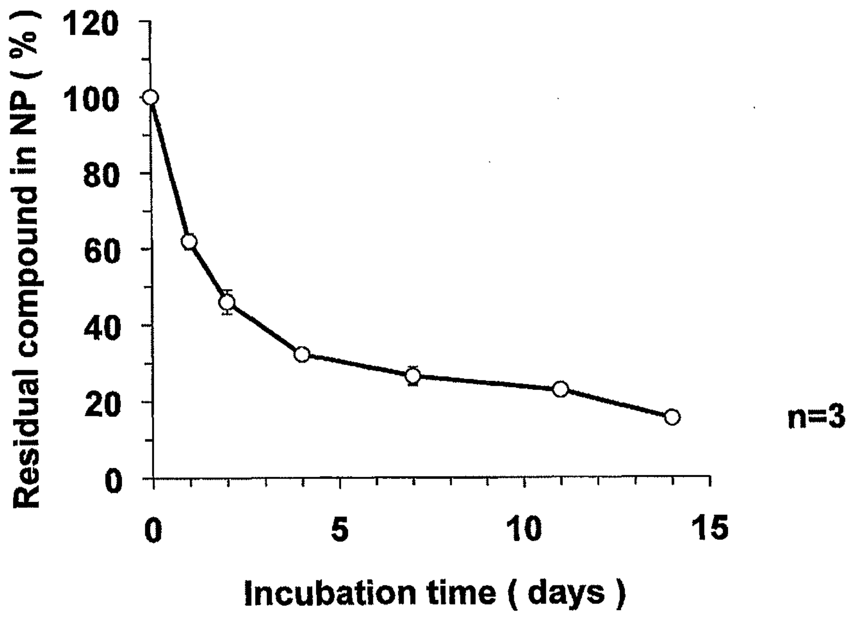
FIG. 4 shows the result of in vitro stability of the beraprost sodium-containing nanoparticle in Example 4.

The result is shown in FIG. 4.

As is also clear from the result shown in the figure, it was confirmed that beraprost sodium was released from the nanoparticle over about 2 weeks.

Beraprost sodium has a biological half-life of about 1.1 hours and also a chemical half-life of 10 days. Preparation of the nanoparticle of the present invention enabled the encapsulated beraprost sodium to be released stably over a longer period compared to these half-lives. In this respect, the present invention is exceptionally unique.

Example 5

Evaluation of Drug Retention in Blood

Either beraprost sodium nanoparticles or beraprost sodium (comparative example) was administered to male Wister rats (5 week old, n=3) intravenously via a tail vein. After administration, a tail vein different from the administration site was cut with a scalpel at specified times, and blood samples were collected by using blood collection tubes (heparin-treated). A sample solution was prepared by adding 50 μL, of the blood to a microfuge tube containing 1,4-dioxane (150 μL). The sample solution was centrifuged (13,200 rpm, 4° C., and 10 minutes), and then, beraprost sodium contained in the supernatant was determined by HPLC.

Figure 5:
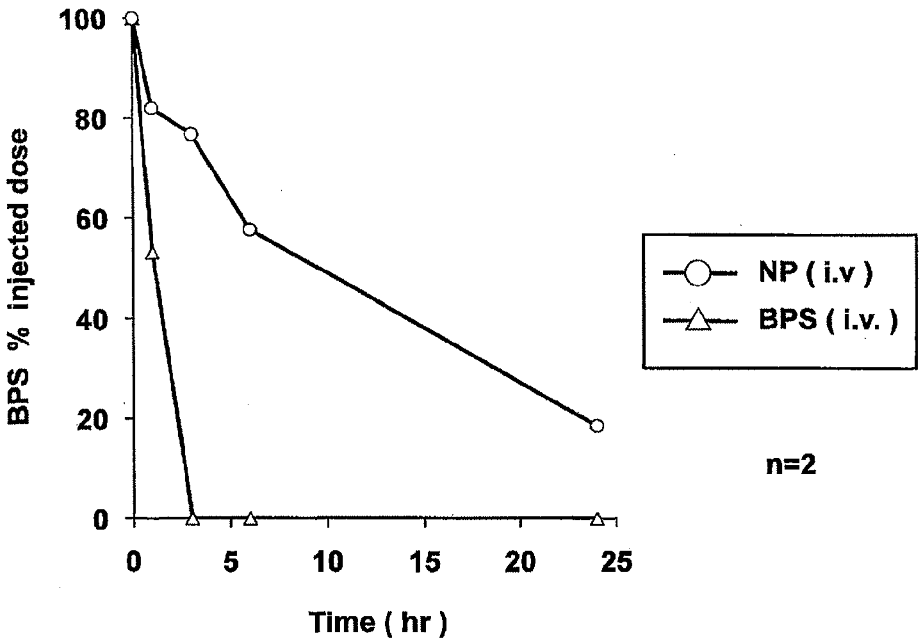
FIG. 5 shows the result of evaluation of the drug retention in the blood in Example 5.

The result is shown in FIG. 5.

As is also clear from the result shown in the figure, it was found that the beraprost sodium-containing nanoparticle of the present invention existed in the blood even 24 hours after its intravenous administration, while little beraprost sodium existed in the blood as early as 3 hours after its administration.

It is understood from this result that the beraprost sodium-containing nanoparticle of the present invention significantly improves the ability of beraprost sodium to remain in the blood.

Example 6

Continuous Increase of cAMP by Administration of Beraprost Sodium-Containing Nanoparticle Prostacyclin leads to relaxation of vascular smooth muscle and exerts a dilation effect on a pulmonary vessel by activating adenyl cyclase via a prostacyclin receptor on the vascular smooth muscle and increasing the concentration of cAMP.

Therefore, the present inventors investigated whether cAMP increased continuously when the beraprost sodium-containing nanoparticle of the present invention was administered.

Either beraprost sodium-containing nanoparticles or beraprost sodium (comparative example) was administered to male Wister rats (5 week old, n=2) intravenously via a tail vein. After administration, a tail vein different from the administration site was cut with a scalpel at specified times, and blood samples were collected by using blood collection tubes. A blood plasma sample was prepared by collecting the blood plasma (supernatant) by centrifugation (2,000 g, 4° C., and 10 minutes). This blood plasma sample was diluted as appropriate and cAMP contained in the blood serum was determined by using a cAMP ELISA kit. The method of measurement followed the protocol made by Assay Designs Inc.

Figure 6:
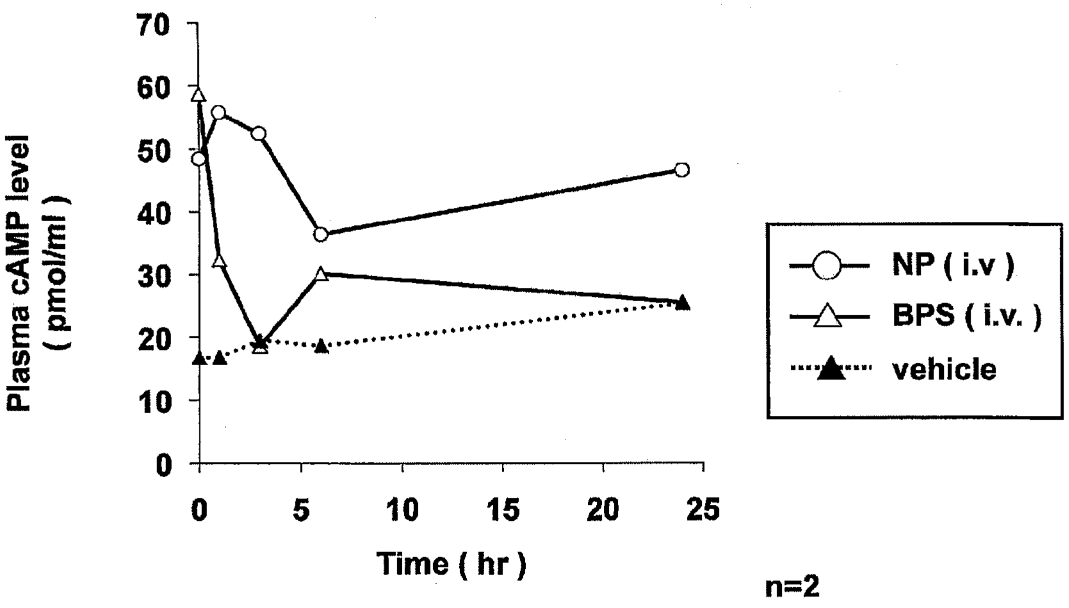
FIG. 6 shows a continuous increase of cAMP resulting from administration of a beraprost sodium-containing nanoparticle in Example 6.

The result is shown in FIG. 6.

As is also clear from the result shown in the figure, continuous increase of cAMP in the plasma was observed even 24 hours after administration of the beraprost sodium-containing nanoparticle of the present invention.

On the other hand, no continuous increase of cAMP was observed after intravenous administration of beraprost sodium. Therefore, it is understood that a continuous pharmacological effect of beraprost sodium may be brought about through preparation of a nanoparticle thereof.

Example 7

Evaluation of Medicinal Effect (Survival Rate) of Beraprost Sodium-Containing Nanoparticle of the Present Invention by Using MCT Disease Model A model animal of MCT (monocrotaline)-induced pulmonary hypertension was used to evaluate the medicinal effect of the beraprost sodium-containing nanoparticle of the present invention.

First, MCT was dissolved in a 1 M hydrochloric acid aqueous solution, and then the solution was neutralized by titrating it with a 1 M sodium hydroxide aqueous solution. The neutral MCT solution thus obtained was used.

Five week old male Wister rats (body weight: 128 to 150 g, n=8 to 12) were anesthetized with pentobarbital (50 mg/kg, intraperitoneal administration) and were injected subcutaneously on the neck with the adjusted MCT solution. Change in the survival rate was monitored for 4 weeks after administration of MCT.

Figure 7:
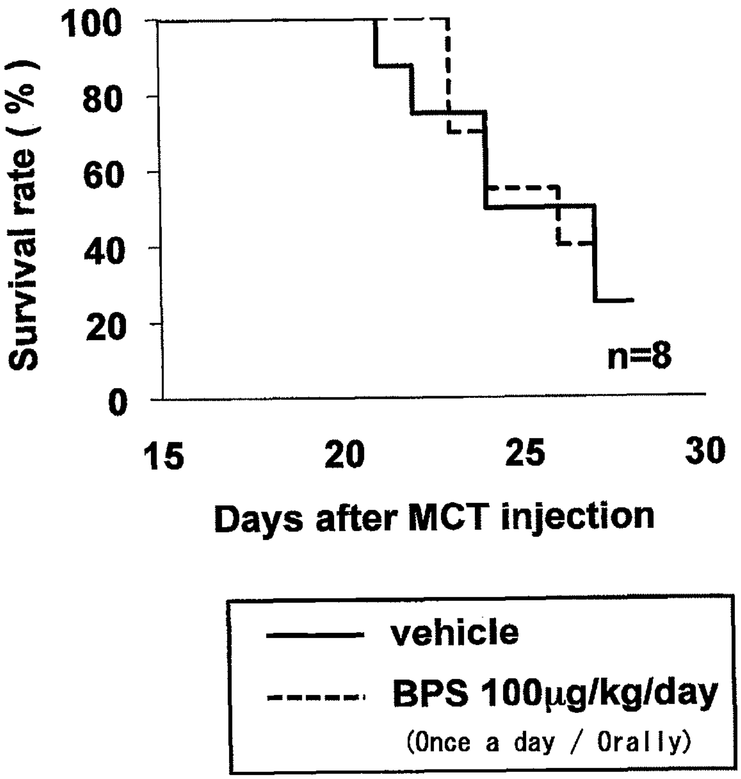
FIG. 7 shows the result of evaluation of the medicinal effect (survival rate) of the beraprost sodium-containing nanoparticle of the present invention by using an MCT disease model in Example 7. This figure shows the results of oral administration of beraprost sodium and administration of a vehicle.
Figure 8:
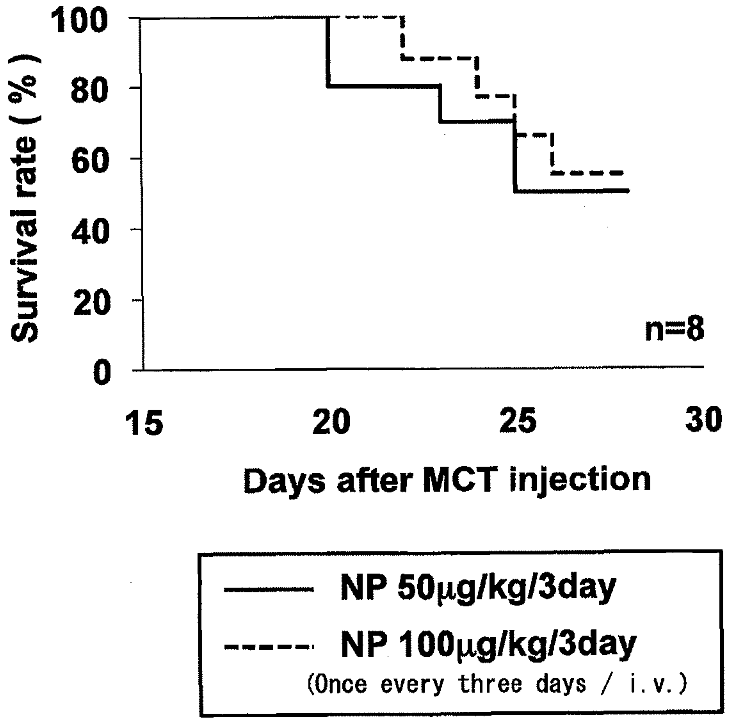
FIG. 8 shows the result of evaluation of the medicinal effect (survival rate) of the beraprost sodium-containing nanoparticle of the present invention by using an MCT disease model in Example V. This figure shows the result of administration of the beraprost sodium-containing nanoparticle of the present invention.

The results are shown in FIG. 7 and FIG. 8.

FIG. 7 shows the results of oral administration of beraprost sodium and administration of a vehicle, while FIG. 8 shows the result of administration of the beraprost sodium-containing nanoparticle of the present invention.

As is clear from comparison of both figures, there was a significant improvement in the survival rate when the beraprost sodium-containing nanoparticle of the present invention was administered intravenously once every three days.

Example 8

Evaluation of Medicinal Effect (Right Ventricular Remodeling, Pulmonary Vessel Hypertrophy) of Beraprost Sodium-Containing Nanoparticle of the Present Invention by Using MCT Disease Model A model animal of MCT (monocrotaline)-induced pulmonary hypertension was used to evaluate the medicinal effect of the beraprost sodium-containing nanoparticle of the present invention.

The rats that were alive 4 weeks after (28 days after) administration of MCT in Example 7 were collected as samples, and their right ventricles were weighed and their hypertrophied pulmonary vessels were quantified.

In other words, the weights of the rats that were alive 4 weeks after administration of MCT were measured, and their hearts and lungs were excised after the rats were sacrificed by exsanguination.

The right ventricle was first cut out from the excised heart, and the septum was removed from the left ventricle to leave only the left ventricle free wall. The weight of each was measured.

Quantification of right ventricular hypertrophy was performed by calculating the percentage of the weight of the right ventricular relative to the body weight. Quantification of the pulmonary vessel hypertrophy was also performed using the excised lung. The lung was immersion fixed in 10% formalin after the excitation of the lung. The lung was embedded in paraffin and sections about 4 μm in thickness were prepared. After the sections were stained with hematoxylin-eosin (HE staining), the sections were examined for the pulmonary vessel hypertrophy by microscopy. The thickness of the tunica media of the pulmonary arteriole was evaluated according to the method by Kay et al. The blood vessels examined were muscular arteries 20 to 200 μm in diameter. Only the blood vessels whose section was a short axis section were measured.

Ten vessels per each specimen were measured. The percentage of the thickness of the blood vessel wall relative to the blood vessel diameter was calculated and used as a measurement of hypertrophy of the tunica media (% wall thickness).

The animals that were alive 4 weeks after administration of MCT were collected as samples, and their right ventricles were weighed and their hypertrophied pulmonary vessels were quantified.

Figure 9:
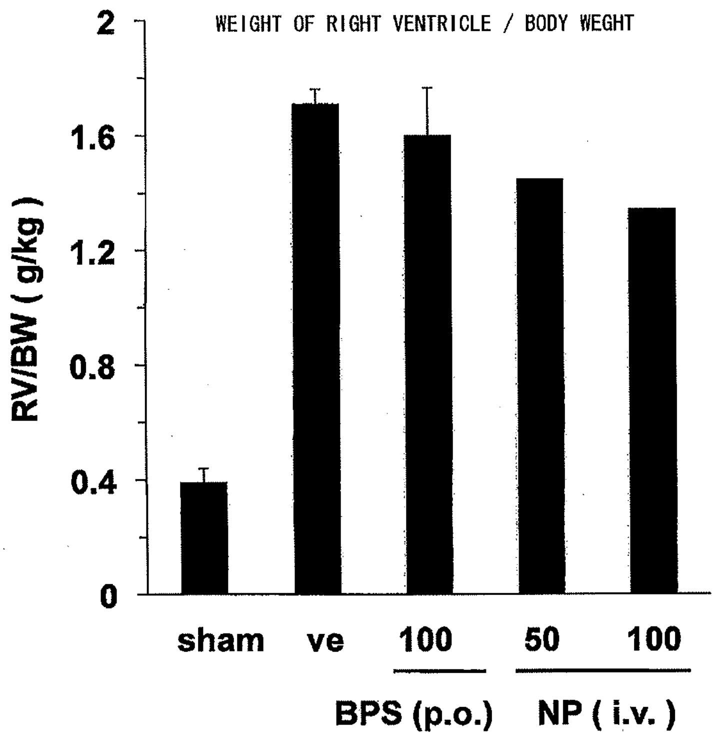
FIG. 9 shows the result of right ventricular remodeling in the evaluation of the medicinal effect of the beraprost sodium-containing nanoparticle of the present invention by using the MCT disease model of Example 8.
Figure 10:
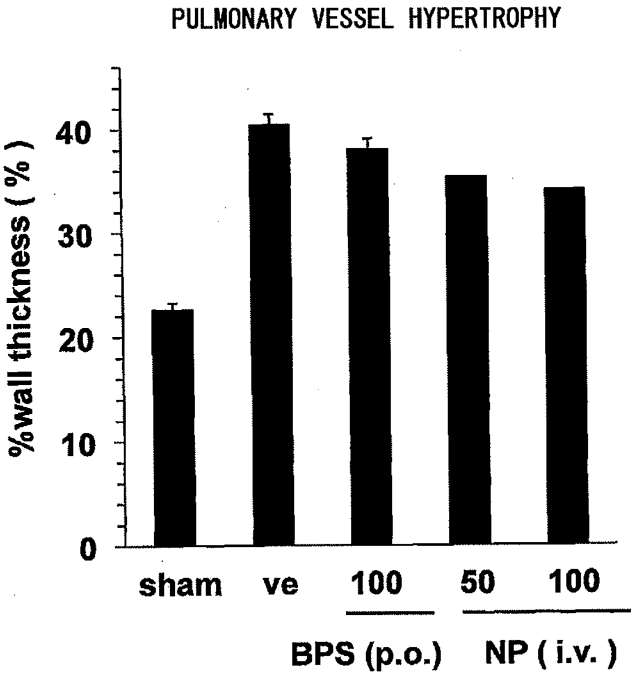
FIG. 10 shows the result of pulmonary vessel hypertrophy in the evaluation of the medicinal effect of the beraprost sodium-containing nanoparticle of the present invention by using the MCT disease model of Example 8.

The results are shown in FIG. 9 and FIG. 10.

FIG. 9 shows the result of the weights of their right ventricles (relative to the total body weight) and FIG. 10 shows their hypertrophied pulmonary vessels.

A significant effect of improving a pathological condition was obtained by administering intravenously the beraprost sodium-containing nanoparticle of the present invention once every three days.

INDUSTRIAL APPLICABILITY

As described above, the beraprost sodium-containing nanoparticle of the present invention excels in sustained release of the drug and moreover has an excellent drug retention in the blood. Therefore, the beraprost sodium-containing nanoparticle is exceptionally unique as an effective formulation of beraprost sodium, which has a short half-life, and serves as a therapeutic agent for pulmonary hypertension that has consideration for QOL of a patient. Thus, the industrial applicability of the beraprost sodium-containing nanoparticle is great.

The invention claimed is:

1. A beraprost sodium-containing nanoparticle for treatment of pulmonary hypertension obtained by:

(a) converting beraprost sodium represented by the following formula (I):

(I)

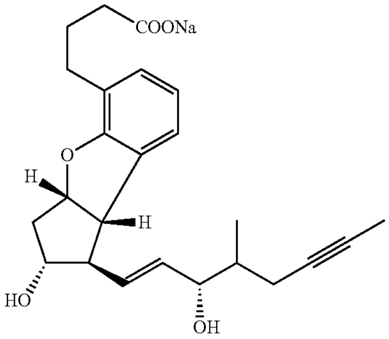

to a hydrophobicized beraprost sodium using a metal ion; and (b) allowing the hydrophobicized beraprost sodium to react with poly-L-lactic acid or a poly(L-lactic acid/glycolic acid) copolymer, and a poly-DL- or L-lactic acid-polyethylene glycol block copolymer or a poly (DL- or L-lactic acid/glycolic acid)-polyethylene glycol block copolymer to obtain a beraprost sodium-containing nanoparticle.

2. The beraprost sodium-containing nanoparticle for treatment of pulmonary hypertension according to claim 1, in which a basic low molecular weight compound is further mixed with the obtained hydrophobicized beraprost sodium.

3. The beraprost sodium-containing nanoparticle for treatment of pulmonary hypertension according to claim 1, wherein the particle has a diameter of 20 to 300 nm.

4. The beraprost sodium-containing nanoparticle for treatment of pulmonary hypertension according to claim 1, wherein the metal ion is one or two or more of an iron ion, a zinc ion, a copper ion, a magnesium ion, a calcium ion, a nickel ion, a beryllium ion, a manganese ion, or a cobalt ion.

5. The beraprost sodium-containing nanoparticle for treatment of pulmonary hypertension according to claim 1, wherein a weight average molecular weight of the poly-DL- or L-lactic acid-polyethylene glycol block copolymer or the poly(DL- or L-lactic acid/glycolic acid)-polyethylene glycol block copolymer is 3,000 to 30,000.

6. The beraprost sodium-containing nanoparticle for treatment of pulmonary hypertension according to claim 2, wherein the basic low molecular weight compound is one or two or more selected from the group consisting of: (dimethylamino)pyridine, pyridine, piperidine, pyrimidine, pyrazine, pyridazine, quinoline, quinuclidine, isoquinoline, bis(dimethylamino)naphthalene, naphthylamine, morpholine, amantadine, aniline, spermine, spermidine, hexamethylenediamine, putrescine, cadaverine, phenethylamine, histamine, diazabicyclooctane, diisopropylethylamine, monoethanolamine, diethanolamine, triethanolamine, ethylamine, diethylamine, triethylamine, methylamine, dimethylamine, trimethylamine, triethylenediamine, diethylenetriamine, ethylenediamine, and trimethylenediamine.

7. A pharmaceutical preparation for treatment of pulmonary hypertension comprising a beraprost sodium-containing nanoparticle, wherein the beraprost sodium-containing nanoparticle is obtained by:

(a) converting beraprost sodium represented by the following formula (I):

(I)

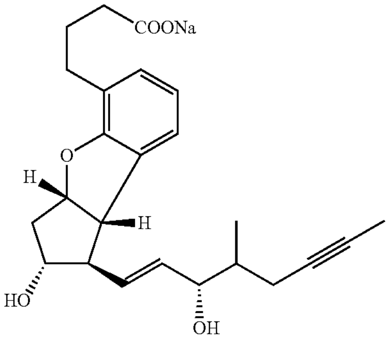

to a hydrophobicized beraprost sodium using a metal ion; and (b) allowing the hydrophobicized beraprost sodium to react with poly-L-lactic acid or a poly(L-lactic acid/glycolic acid) copolymer, and a poly-DL- or L-lactic acid-polyethylene glycol block copolymer or a poly (DL- or L-lactic acid/glycolic acid)-polyethylene glycol block copolymer to obtain a beraprost sodium-containing nanoparticle.

8. The pharmaceutical preparation for treatment of pulmonary hypertension comprising the beraprost sodium-containing nanoparticle recited in claim 7, in which a basic low molecular weight compound is mixed with the obtained hydrophobicized beraprost sodium.

9. The pharmaceutical preparation for treatment of pulmonary hypertension comprising the beraprost sodium-containing nanoparticle recited in claim 7, wherein the particle has a diameter of 20 to 300 nm.

10. The pharmaceutical preparation for treatment of pulmonary hypertension comprising the beraprost sodium-containing nanoparticle recited in claim 7, wherein the metal ion is one or two or more of an iron ion, a zinc ion, a copper ion, a magnesium ion, a calcium ion, a nickel ion, a beryllium ion, a manganese ion, or a cobalt ion.

11. The pharmaceutical preparation for treatment of pulmonary hypertension comprising the beraprost sodium-containing nanoparticle recited in claim 7, wherein a weight average molecular weight of the poly-DL- or L-lactic acid-polyethylene glycol block copolymer or the poly(DL- or L-lactic acid/glycolic acid)-polyethylene glycol block copolymer is 3,000 to 30,000.

12. The pharmaceutical preparation for treatment of pulmonary hypertension comprising the beraprost sodium-containing nanoparticle recited in claim 8, wherein the basic low molecular weight compound is one or two or more selected from the group consisting of: (dimethylamino)pyridine, pyridine, piperidine, pyrimidine, pyrazine, pyridazine, quinoline, quinuclidine, isoquinoline, bis(dimethylamino)naphthalene, naphthylamine, morpholine, amantadine, aniline, spermine, spermidine, hexamethylenediamine, putrescine, cadaverine, phenethylamine, histamine, diazabicyclooctane, diisopropylethylamine, monoethanolamine, diethanolamine, triethanolamine, ethylamine, diethylamine, triethylamine, methylamine, dimethylamine, trimethylamine, triethylenediamine, diethylenetriamine, ethylenediamine, and trimethylenediamine.

13. A formulation for parenteral administration in a form of an intravenous injection formulation or a local injection formulation, wherein the formulation comprises a pharmaceutical preparation for treatment of pulmonary hypertension comprising a beraprost sodium-containing nanoparticle, wherein the beraprost sodium-containing nanoparticle is obtained by:

(a) converting beraprost sodium represented by the following formula (I):

(I)

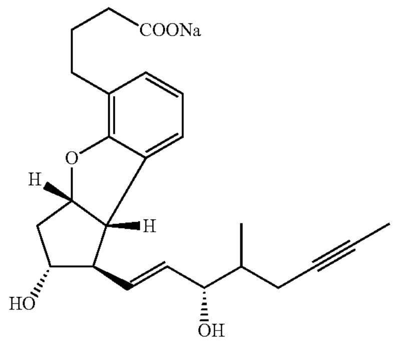

to a hydrophobicized beraprost sodium using a metal ion; and (b) allowing the hydrophobicized beraprost sodium to react with poly-L-lactic acid or a poly(L-lactic acid/glycolic acid) copolymer, and a poly-DL- or L-lactic acid-polyethylene glycol block copolymer or a poly (DL- or L-lactic acid/glycolic acid)-polyethylene glycol block copolymer to obtain a beraprost sodium-containing nanoparticle.

14. The formulation for parenteral administration recited in claim 13, in which a basic low molecular weight compound is mixed with the obtained hydrophobicized beraprost sodium.

15. The formulation for parenteral administration recited in claim 13, wherein the particle has a diameter of 20 to 300 nm.

16. The formulation for parenteral administration recited in claim 13, wherein the metal ion is one or two or more of an iron ion, a zinc ion, a copper ion, a magnesium ion, a calcium ion, a nickel ion, a beryllium ion, a manganese ion, or a cobalt ion.

17. The formulation for parenteral administration recited in claim 13, wherein a weight average molecular weight of the poly-DL- or L-lactic acid-polyethylene glycol block copolymer or the poly(DL- or L-lactic acid/glycolic acid)-polyethylene glycol block copolymer is 3,000 to 30,000.

18. The formulation for parenteral administration recited in claim 14, wherein the basic low molecular weight compound is one or two or more selected from the group consisting of: (dimethylamino)pyridine, pyridine, piperidine, pyrimidine, pyrazine, pyridazine, quinoline, quinuclidine, isoquinoline, bis(dimethylamino)naphthalene, naphthylamine, morpholine, amantadine, aniline, spermine, spermidine, hexamethylenediamine, putrescine, cadaverine, phenethylamine, histamine, diazabicyclooctane, diisopropylethylamine, monoethanolamine, diethanolamine, triethanolamine, ethylamine, diethylamine, triethylamine, methylamine, dimethylamine, trimethylamine, triethylenediamine, diethylenetriamine, ethylenediamine, and trimethylenediamine.

* * * * *